United States Patent [19]

Cipriani et al.

[11] 4,116,997

[45] Sep. 26, 1978

[54] METHOD FOR THE PREPARATION OF CARBONIC ACID MONOESTER SALTS

[75] Inventors: Gioacchino Cipriani; Carlo Neri, both of San Donato Milanese, Italy

[73] Assignee: Anic, S.p.A., Palermo, Italy

[21] Appl. No.: 800,045

[22] Filed: May 24, 1977

Related U.S. Application Data

[63] Continuation of Ser. No. 639,444, Dec. 10, 1975, abandoned.

[30] Foreign Application Priority Data

Dec. 10, 1974 [IT] Italy ................................ 30338 A/74

[51] Int. Cl.$^2$ .............................................. C07C 68/04
[52] U.S. Cl. ................................ 260/463; 260/465 K; 544/299
[58] Field of Search ......................................... 260/463

[56] References Cited

PUBLICATIONS

Z. Anorg. Allg. Chem. 397, 237–246 (1973), Behrendt et al.
Chemical Abstracts, 76, (1972) 85305v.

*Primary Examiner*—Lewis Gotts
*Assistant Examiner*—Molly C. Eakin
*Attorney, Agent, or Firm*—Morgan, Finnegan, Pine, Foley & Lee

[57] ABSTRACT

A method is disclosed for the preparation of salts of monoesters of the carbonic acid, the improvement consisting in that the alcohols corresponding to the esters are reacted with carbon dioxide and a compound of an alkali metal or an alkaline earth metal. A distinct advantage over the use of the alcoholates is obtained inasmuch as the reaction is less violent, side-reactions are put aside and the costs are lowered.

2 Claims, No Drawings

METHOD FOR THE PREPARATION OF CARBONIC ACID MONOESTER SALTS

This is a continuation of application Ser. No. 639,444 filed Dec. 10, 1975, now abandoned.

This invention relates to a method for the preparation of salts of monoesters of the carbonic acid, having the forumla:

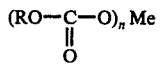

wherein R is an alkyl, aryl, cycloalkyl or aralkyl radical, either plain or substituted, either mono- or polyhydroxylated, either saturated or unsaturated, $n$ is 1 or 2, and Me is an alkali metal or an alkaline earth metal, the method comprising the step of reacting the corresponding alcohols with carbon dioxide and a compound of the metal having the formula $Me_mX_n$ wherein X is selected from $CO_3^{--}$, $SO_3^{--}$, $O^{--}$, $OH^-$, $BO_3^{---}$, $S^{--}$, $SH^-$, etc. and $m$ is 1, 2, or 3, $n$ having the above indicated values.

The reaction, which takes place according to the following pattern:

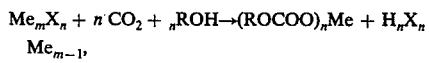

simply takes place by causing a stream of $CO_2$ to bubble through a solution or a suspension of the selected salt in the alcohol concerned, preferably with stirring. The pressure of $CO_2$ can be varied between 0 and 100 atmospheres, whereas the temperature is maintained between the freezing and the boiling point temperature of the alcohol, preferably between 0° C. and 60° C.

It is also possible to operate in the presence of any solvent whatsoever providing that it is inert to the ends of the subject reaction.

The salts of the carbonic acid monoesters can be isolated by filtration, should they be insoluble, or precipitated with an appropriate solvent, or, lastly, by evaporating off the reaction medium.

Such salts can be used in lieu of the corresponding alcoholates in the condensation reactions, for example in the condensations of aldehydes with active-hydrogen-containing molecules, or of esters with ureas, or also as the catalysts in the aromatic aldehyde disproportionation reactions.

As compared with the alcoholates, the salts as obtained according to the present invention unfold, in the above indicated reactions, a less drastic action, the side reactions being limited and lower costs being achieved.

The foregoing considerations will become more clearly apparent from the scrutiny of the following examples, which are intended to elucidate the invention without, however, limiting the same thereby.

EXAMPLE 1

10 Grams of anhydrous $K_2CO_3$ are slurried in 100 mls anhydrous methanol and a stream of $CO_2$ for an amount slightly over that which is absorbed is caused to bubble therethrough with vigorous stirring at 25° C.

The reaction is both exothermic and rapid and is completed within 30 mins. On completion of the absorption, the residue, $KHCO_3$, is collected on a filter and the solution is evaporated in a vacuo. There are obtained 8.5 grams of impure $KOCOOCH_3$, as it contains traces of $KHCO_3$.

EXAMPLE 2

5.6 Grams of CaO are slurried in 100 mls allyl alcohol and stirred at 25° C. under a stream of $CO_2$. A reaction which is both exothermic and rapid is obtained and is completed within 35 mins. The bulky white precipitate is collected on a filter under a nitrogen blanket, washed with ethyl ether and dried in a vacuo. There are obtained 20 grams of $Ca(OCOOCH_2CH=CH_2)_2$.

EXAMPLE 3

10 Grams of $NaOCOOCH_3$ (0.1 mol) are dissolved in 100 mls methanol: 16 grams of diethylmalonate and 6 grams urea are added thereto. The mixture is refluxed during about 8 hours, then is dried in a vacuo to obtain 15 grams (approx.) of the sodium salt of the barbituric acid. The latter, upon hydrolysis with 2 N hydrochloric acid and extraction with ether gives 12 grams of barbituric acid.

EXAMPLE 4

12 Grams of benzyl cyanide and 11 grams of benzaldehyde with 10 grams of $NaOCOOCH_3$ are dissolved in 100 mls methanol and refluxed during two hours. The sodium carbonate is collected, hot, on a filter and the solvent is evaporated in a vacuo. There are obtained 22 grams of phenylcinnamonitrile, having $Na_2CO_3$ as an impurity. The pure product is obtained by washing with water.

What we claim is:

1. A method for the preparation of $KOCOOCH_3$ by the process which consists of reacting $K_2CO_3$ with an excess of $CO_2$ and methanol.

2. A method for the preparation of $Ca(OCOOCH_2CH=CH_2)_2$ by the process which consists of reacting CaO with an excess of $CO_2$ and allyl alcohol.